United States Patent [19]

Olsson et al.

[11] Patent Number: 5,423,313

[45] Date of Patent: Jun. 13, 1995

[54] RESPIRATOR INTENDED FOR CONNECTION TO HUMAN OR ANIMAL AIRWAYS

[75] Inventors: Sven-Gunnar Olsson, Arloev; Bjorn Jonson, Lund, both of Sweden

[73] Assignee: Siemens-Elema AB, Solna, Sweden

[21] Appl. No.: 890,291

[22] PCT Filed: Mar. 9, 1982

[86] PCT No.: PCT/SE82/00063

§ 371 Date: Oct. 19, 1982

§ 102(e) Date: Oct. 19, 1982

[87] PCT Pub. No.: WO82/03014

PCT Pub. Date: Sep. 16, 1982

Related U.S. Application Data

[63] Continuation of Ser. No. 816,850, Jan. 2, 1992, abandoned, which is a continuation of Ser. No. 512,524, Apr. 18, 1990, abandoned, which is a continuation of Ser. No. 418,709, Oct. 3, 1989, abandoned, which is a continuation of Ser. No. 309,994, Feb. 13, 1989, abandoned, which is a continuation of Ser. No. 180,679, Apr. 8, 1988, abandoned, which is a continuation of Ser. No. 4,763, Jan. 6, 1987, abandoned, which is a continuation of Ser. No. 834,658, Feb. 27, 1986, abandoned, which is a continuation of Ser. No. 438,888, Oct. 19, 1982, abandoned.

[30] Foreign Application Priority Data

Oct. 3, 1981 [SE] Sweden ............................ 8101488

[51] Int. Cl.[6] .................... A61M 16/00; A61M 15/00; A62B 7/00; A62B 9/02
[52] U.S. Cl. ...................... 128/204.21; 128/204.22; 128/204.23; 128/204.28; 128/205.23; 128/205.24; 128/207.15; 128/207.16; 128/203.14; 128/203.16
[58] Field of Search ............... 128/204.18, 204.21, 128/204.22, 204.23, 204.25, 204.24, 204.19, 204.26, 207.14–207.16, 203.16, 203.12, 203.14, 203.27; 137/205.23, 205.24, 399

[56] References Cited

U.S. PATENT DOCUMENTS

| 2,780,222 | 2/1957 | Polzin et al. |  |
|---|---|---|---|
| 3,191,596 | 6/1965 | Bird et al. | 128/204.26 |
| 3,221,733 | 12/1965 | Beasley . |  |

(List continued on next page.)

FOREIGN PATENT DOCUMENTS

| 48207 | 7/1982 | Netherlands | 128/207.18 |
|---|---|---|---|
| 7315392 | 11/1973 | Sweden . |  |
| 7401676 | 2/1974 | Sweden . |  |
| 7906135 | 7/1979 | Sweden . |  |
| 1364641 | 8/1974 | United Kingdom | 128/204.21 |
| 2063686 | 6/1981 | United Kingdom | 128/204.25 |
| 2093218 | 8/1982 | United Kingdom | 128/207.15 |
| 2113101 | 8/1983 | United Kingdom | 128/207.15 |

OTHER PUBLICATIONS

"A New Anesthesia Delivery System," Cooper et al., Anesthesiology, vol. 49, pp. 510–518 (1978).

McPherson, Respiratory Therapy Equipment, pp. 351–358 (1977).

(List continued on next page.)

*Primary Examiner*—Randall L. Green
*Assistant Examiner*—Kimi Reichle
*Attorney, Agent, or Firm*—Hill, Steadman & Simpson

[57] ABSTRACT

This invention comprises a respirator intended for connection to human or animal airways. A first device for supplying and receiving respiratory gas to and from the airways so that the lungs can be ventilated is combined with a second devices that provides a valve-regulated separate supply of gas to the airways independently of the respiratory gas flow provided by the first device. The second device incorporates at least one line used to supply gas under pressure. Furthermore there are a number of valves connected in parallel to this line, which provide a pulsating gas supply, and a control unit that can be used to control at least some of the gas pulse characteristics.

21 Claims, 3 Drawing Sheets

U.S. PATENT DOCUMENTS

| | | |
|---|---|---|
| 3,221,734 | 12/1965 | Beasley . |
| 3,265,061 | 8/1966 | Gage, Jr. . |
| 3,316,902 | 5/1967 | Winchel et al. . |
| 3,362,404 | 1/1968 | Beasley . |
| 3,368,555 | 2/1968 | Beasley . |
| 3,385,295 | 5/1968 | Beasley . |
| 3,523,527 | 8/1970 | Foster .............................. 128/204.21 |
| 3,534,753 | 10/1970 | Ollivier . |
| 3,628,532 | 12/1971 | Magrath ........................ 128/204.25 |
| 3,688,770 | 9/1972 | O'Neill ........................... 128/204.25 |
| 3,695,263 | 10/1972 | Kilping . |
| 3,741,208 | 6/1973 | Jonsson et al. . |
| 3,769,967 | 11/1973 | Jones et al. ........................ 128/684 |
| 3,830,256 | 8/1974 | Cox .................................... 137/599 |
| 3,886,971 | 6/1975 | Lundsgaard ........................ 137/599 |
| 3,923,055 | 12/1975 | Hammacher .................. 128/204.23 |
| 3,993,059 | 11/1976 | Sjostrand ........................ 128/205.24 |
| 4,155,356 | 5/1979 | Venegas ............................. 128/145 |
| 4,256,100 | 3/1981 | Levy et al. ..................... 128/204.21 |
| 4,265,237 | 5/1981 | Schwanbom et al. .......... 128/204.25 |
| 4,270,530 | 6/1981 | Baum et al. ..................... 128/204.25 |
| 4,351,329 | 9/1982 | Ellestad et al. ................ 128/204.21 |
| 4,425,914 | 1/1984 | Ray et al. ........................ 128/200.14 |
| 4,450,838 | 5/1984 | Modownik ..................... 128/204.23 |
| 4,463,756 | 8/1984 | Thuc ................................ 128/204.21 |
| 4,481,944 | 11/1984 | Bunnell ........................... 128/204.18 |
| 4,495,946 | 1/1985 | Lemer ............................. 128/204.25 |

OTHER PUBLICATIONS

Effective Pulmonary Ventilation with Small-Volume Oscillations at High Frequency, Science, vol. 29, pp. 609–611 Aug. 1980.

Klain et al, High Frequency Percutaneous Transtracheal Jet Ventilation, Critical Care Medicine, vol. 5, No. 6, pp. 280–287 (1977).

Erickson et al, Effects of High Frequency Positive–Pressure Ventilation (HFPPV) and General Anesthesia on Intrapulmonary Gas Distribution in Patients Undergoing Diagnostic Bronchoscopy, Anesthesia and Analgesia, vol. 59, No. 8, pp. 585–593 (Aug. 1980).

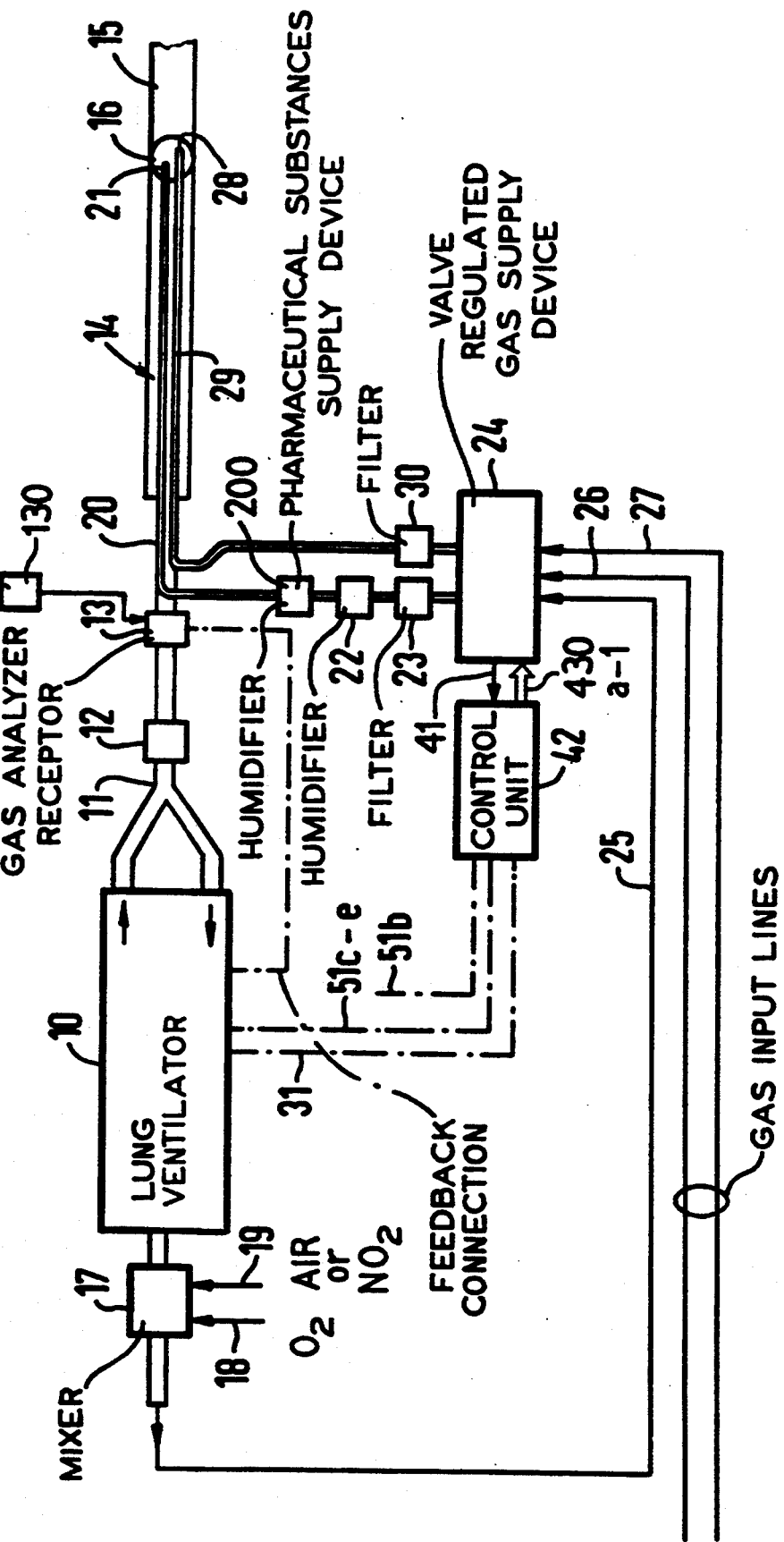

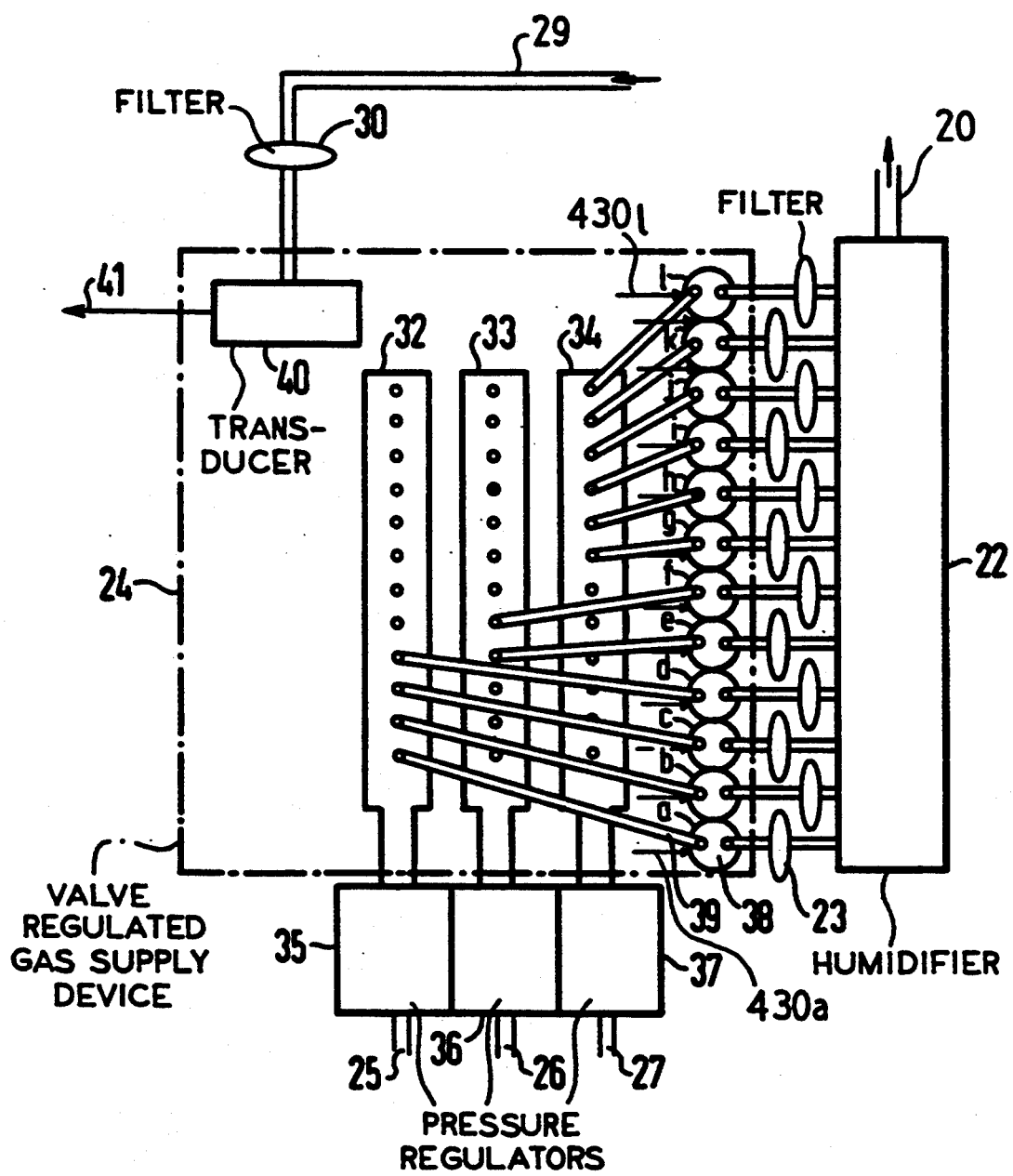

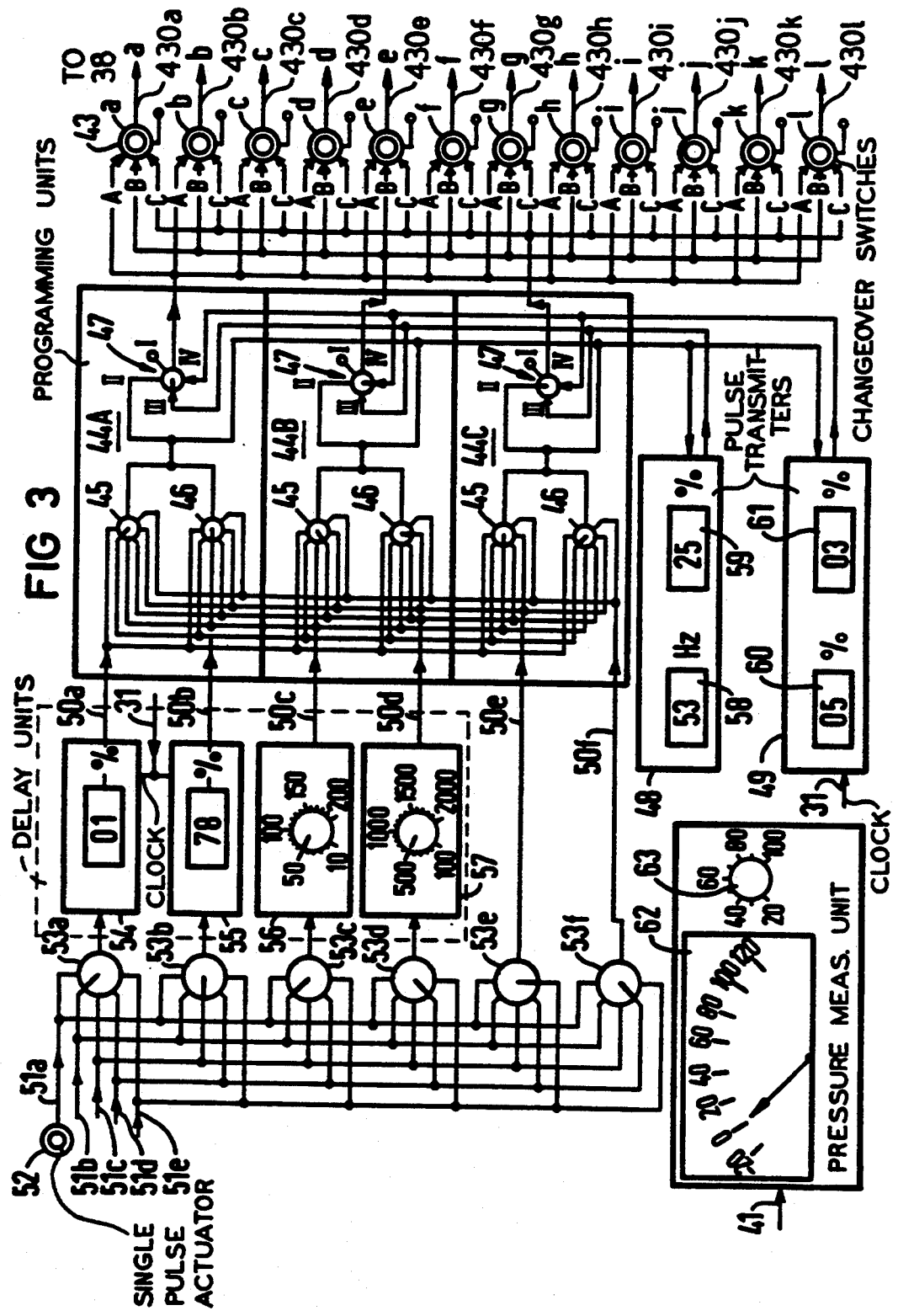

RESPIRATOR INTENDED FOR CONNECTION TO HUMAN OR ANIMAL AIRWAYS

This is a continuation of application Ser. No. 816,850 filed Jan. 2, 1992 (now abandoned), which is a continuation of application Ser. No. 512,524 filed Apr. 18, 1990 (now abandoned), which is a continuation of application Ser. No. 418,709 filed Oct. 3, 1989 (now abandoned), which is a continuation of application Ser. No. 309,994 filed Feb. 13, 1989 (now abandoned),which is a continuation of application Ser. No. 004,763 filed Jan. 6, 1987 (now abandoned), which is a continuation of application Ser. No. 834,658 filed Feb. 27, 1986 (now abandoned), which is a continuation of application Ser. No. 438,888 filed Oct. 19, 1982 (now abandoned).

BACKGROUND OF THE INVENTION

1. Field of the Invention

This invention is directed to a respirator intended for connection to human or animal airways.

2. Description of the Prior Art

Conventional respirator treatment makes use of frequencies and tidal volumes which correspond to those encountered in a patient who is breathing spontaneously. In this connection, however, it is difficult in some patients to obtain a satisfactory gas exchange in all parts of the lungs without having to apply injurious pressure which can cause a rupture or affect the blood vessels in such a way as to inhibit blood circulation through the lungs.

To avoid such injurious pressures and provide more uniform ventilation of the lungs, certain proposals for respirator design have been made previously.

One previously known respirator (AGA Bronchovent, AGA Medical AB, Lidingo, 1 Sweden) is equipped with a tracheal main tube which is provided with a branch tube used to supply the respiratory gas at a pressure of up to 1 kg/cm$^2$ to the tracheal main tube passage through which the respiratory gas flows, whereupon the branch tube opens into the tracheal main tube via a restrictor which provides high flow resistance. This respirator is said to be more effective than a conventional respirator, probably due to the fact that the respiratory gas is supplied in such a way that turbulence builds up, thereby enhancing gas diffusion. It is also said that it provides better mucus transport and reduces the tendency toward spontaneous breathing. This known respirator, however, entails risk for the patient because of the high pressure that is applied to the respiratory gas. Moreover, it is difficult to humidify the respiratory gas. For this previously known respirator, the breathing frequency has been increased to approximately two breaths per second as compared with a normal breathing rate of $\frac{1}{2}$-$\frac{1}{4}$ breaths per second, and this results in smaller tidal volumes and lower pressure in the lungs., The improved ventilation is probably attributable to the turbulence that occurs in the respiratory gas. For a more detailed description of this known respirator, refer to Anesthesia and Analgesia, Vol. 59, No. 8, August 1980, p. 594–603.

Another previously proposed respirator (Klain Jet Ventilator, Acutronic AG, Jona, Switzerland) uses is called jet injection. Here, gas exchange in the lungs is accomplished by means of a gas jet that is supplied to the lungs in pulses having a frequency of up to 40 Hz through a passage in the tracheal tube or through a slender cannular tube placed directly in the trachea, while expiratory gas leaves the lungs via another passage in the tracheal tube or through the trachea. This respirator provides uniform and low pressure in the lungs, and this is advantageous in connection with surgery, because there is no movement of the thorax and there is minimal effect on blood circulation through the lungs. A respirator of this design, however, has many disadvantages. The gas jet can injure and, in the worst case, penetrate the mucous membranes in the trachea, and it can injure the cilia. It is difficult to humidify the respiratory gas, and it is impossible to ascertain whether or not ventilation is taking place by observing the movement of the chest. Here, there is no easy way to determine how much of the respiratory gas has been in the lungs or to measure the composition of the gas in the alveoli. For information about this respirator, refer to Crit. Care Med. 5:280–287, 1977.

Finally, a respirator has been proposed for which the tracheal tube comprises intersecting tubes through which the respiratory gas passes continuously. A pulsator which operates at right angles to the flowing gas transports the gas through the tracheal duct passage at a frequency of up to 40 or 50 Hz. As far as it is known, this respirator has thus far only been used on an experimental basis for animals and not on humans. Increased transport of mucus was herewith observed, but it has been impossible to check the effect of ventilation, and the effect of the high frequencies on blood circulation and biological substances is unknown. For further information, refer to Proc. Am. Exp. Biol. 38 (part II): 951, 1979; and to Science, Vol. 209, 609 and 610, 1980.

In addition to the aforementioned disadvantages, long-term high frequency ventilation, which occurs in connection with (for example) jet injection and the pulsator method, is disadvantageous due to the fact that the functioning of the lungs deteriorates. For example, the lungs become stiffer and the oxygenation of arterial blood deteriorates, and as a result fluids can accumulate in the pleural sac.

SUMMARY OF THE INVENTION

The primary objective of this invention is to provide a respirator intended for connection to human or animal airways which can ventilate the patient in the conventional manner (i.e., ventilation according to a normal respiratory cycle having a normal breathing rate to simulate spontaneous breathing), and which also provides optimal and reliable application of any one of the new techniques for which application attempts were made in connection with the aforementioned ventilation principles, and which also permits the combining of old and new techniques. The respirator disclosed and claimed permits adequate and suitably distributed alveolar ventilation of the patient's lungs, meaning that ventilation is controllable with regard to volume and composition of the respiratory as with small tidal breathing movements, i.e. with the desired small respiratory volumes and thus low pressure in the airways, so that the lungs and airways are protected, particularly in patients with stiff lungs and so that there is only a slight effect on the blood vessels and the associated inhibition of blood circulation through the lungs, without entailing the disadvantages of the known respirators.

A second objective is to provide a respirator with which gases having a specified composition can be added to the respiratory gas in an accurately quantifiable manner (supply can be determined with regard to volume and time), so that by analyzing the respiratory gas that is expired, it will be possible to draw conclusions regarding the manner in which the lungs are functioning.

Another objective of the invention is to provide a respirator for accurate metering of the supply of therapeutical or otherwise pharmaceutically active substances with regard to quantity and time in the breathing cycle. For example, anaesthetic gases can be added to the gas mixture delivered to the patient in pulses, and such pulses can have a higher concentration of the anaesthetic gas than that normally permitted in the respiratory gas. Because the concentration of the anaesthetic gas is proportional to the concentration in the respiratory gas that is expired, the dosage can be easily controlled by measuring the aforesaid concentration in the alveolar gas when, as it is being expired, it reaches the airway opening, and by adapting the anaesthetic gas pulses in the inspired gas to the extent required.

Another objective of the invention is to provide a means for measuring the alveolar gas concentration even when the aforesaid new techniques are applied to enhance gas exchange in the lungs.

Finally, the invention disclosed and claimed herein is a respirator so arranged that during the end of expiration, the expiratory gas in the tracheal tube or the line connected to the Y-fitting on the ventilator can be flushed out using fresh or unused respiratory gas to prevent the used respiratory gas from re-entering the patient's alveolar space.

BRIEF DESCRIPTION OF THE DRAWINGS

The invention will be explained in greater detail in the following paragraphs which are written with reference to the attached drawings where:

FIG. 1 is a schematic drawing of the respirator that comprises this invention

FIG. 2 is a schematic diagram of the device used in the respirator to provide a valve-regulated separate supply of gas to the airways, and FIG. 3 is a circuit diagram of the system used to control the valves in the device shown in FIG. 2.

DESCRIPTION OF THE PREFERRED EMBODIMENTS

With reference to the diagram shown in FIG. 1, a first lung ventilator 10, which may be a servoventilator of type 900B made by SIEMENS-ELEMA AB, Solna, Sweden, for example, is connected to Y-tube 11, which via humidifier 12, which may be, for example, a servohumidifier 150 made by SIEMENS-ELEMA AB, Solna, Sweden, and a receptor 13 for a gas analyzer 130, which may be, for example, a type 930 made by SIEMENS-ELEMA AB, Solna, Sweden, is joined to tracheal tube 14. The tracheal tube 14 is to be inserted in the trachea which is indicated by 15, and can at one end—the end that is to be inserted into the trachea—be provided with an expandable sleeve 16 of known design to provide a seal between the outside of the tracheal tube 14 and the inside of the trachea. It is not necessary to have such a seal; instead, the tracheal tube 14 can be inserted relatively loosely into the trachea. Moreover, it shall be noted that the tracheal tube 14 can be replaced with a hose that joins lung ventilator 10 to a breathing mask of the conventional type that is designed to be applied over the patient's nose and mouth. The lung ventilator operates in the known manner to supply and lead away the respiratory gas to and from the airways via tracheal tube 14 in order to ventilate the lungs. The respiratory gas is supplied to the lung ventilator from a mixer 17 that mixes the respiratory gas and is connected to a line 18 that carries pure oxygen ($O_2$) and also to a line 19 that carries air or nitrous oxide.

Tracheal tube 14 contains a passage or line 20 which is separated from the rest of the passage through the tracheal tube 14, i.e. from the passage that carries the respiratory gas obtained from lung ventilator 10, and this line 20 opens into the inside end of the tracheal duct at 21. This line, via humidifier 22 and a sterile filter 23, is connected to a device 24' such as a second lung ventilator, that provides a valve-regulated separate supply of gas to line 20, regardless of the rate of flow of the respiratory gas which passes through the tracheal duct and is controlled by lung ventilator 10, but is nonetheless coordinated with the aforesaid rate of flow and/or breathing movements of the patient being treated by the respirator. Device 24 is connected to gas mixer 17 via line 25, but it is also connected to lines 26 and 27 and can be connected to the desired number of additional lines that supply respiratory gas at a pressure other than that of the respiratory gas obtained from the gas mixer, and it is also used to supply gases of different types than the respiratory gas such as a test gas, anaesthetic gas or gas that is therapeutically active. Device 24 includes means for regulating the supply of gas through line 20, to pulsate this gas flow for example, and this regulation can be implemented in different ways depending on different regulation parameters which will be described below.

Pressure intake 28 is provided in the inside end of tracheal tube 14, and this pressure intake communicates with the passage or line 29 in the tracheal tube 14 which, like line 20, is separated from the rest of the passage through the tracheal duct and is connected via sterile filter 30 and transducer 40 (FIG. 2) to device 42 in order to control this device 24, depending upon the pressure at the inside end of the tracheal duct In addition, device 42 is connected, via an electrical connection, to lung ventilator 10 in order to control device 24, depending upon the functioning of the lung ventilator during coordination of the gas supply regulated by device 24 with the flow of respiratory gas obtained from the lung ventilator and/or with the patient's breathing movements, as described in greater detail in the following paragraphs.

Opening 21 which is used for the supply of gas from device 24 can, like pressure intake 28, be arranged in a hose running to a breathing mask or tracheal tube of the conventional design or arranged anywhere in the passage through which the respiratory gas flows, although preferably as close to the patient's lungs as possible.

A device 200 can be provided for the supply of pharmaceutically active substances to the gas passing through line 20, for example in the form of nozzles that supply substances in liquid form.

The manner in which device 24 is controlled will be explained in greater detail below, however, the design and construction of device 24 will first be described with reference to FIG. 2.

Lines 25, 26 and 27 are each connected to one of three distributors 32, 33 and 34 via one of three pressure regulators 35, 36 and 37. These pressure regulators can perhaps be omitted if sources of gas at suitable pressure are available. A number of miniature solenoid valves 38a–38l are provided, and these valves can be, for example, of type LIF LF AA 1200118H made by the Lee Company, Westbrook, Conn., USA. These valves are connected, via hoses 39 provided with quick couplings, to the distributors such that valves 38a–38d are connected to distributor 32, valves 38e and 38f are connected to distributor 33 and valves 38g–38l are connected to distributor 34, although it is possible to connect the valves in some other configuration, thus permitting an arbitrary number of valves to be connected to the desired distributor. Instead of hoses 39 with quick couplings, permanent connections with or without multiway valves can be provided between solenoid valves 38a–38l and distributors 32, 33 and 34, and it is also possible to have all connections on each distributor provided with solenoid valves so that reconnection is not necessary. Each solenoid valve has its own individual sterile filter 23 which connects it to humidifier 22.

The purpose of joining each of lines 25, 26 and 27 to line 20 via two or more miniature solenoid valves is threefold: first, it permits gas flow from any of lines 25, 26 or 27 to line 20 to be regulated by opening one or more of the valves 38 connected to the line in question, i.e. 25, 26 or 27; secondly, gas flow from line 25, 26 or 27, on condition that the gas pressure is very high relative to the pressure in line 20, can be started and stopped quickly in order to provide pulses at very high frequency—in practice, up to 100 Hz—and to permit fast regulation of the flow or pressure due to the fact that the movable parts in these miniature solenoids valves have very low mass; and thirdly, risk that the patient will be injured as a result of a mechanical or electrical malfunction of an individual valve is eliminated. With regard to the last point mentioned, the aforesaid purpose is achieved due to the fact that the flow channel in each miniature solenoid valve is narrow so that only a limited flow can pass through, and this means that a high pressure cannot build up quickly in the patient if a valve were to remain in its open position when it actually should be closed. This provides time for the existing safety devices in the lung ventilator to go into operation and open a passage to the external air and issue an alarm to the personnel who are responsible for respirator treatment. And, conversely, gas is supplied even if one valve of the two or more that are connected in parallel were to remain in the closed position when it actually should be open.

Valves 38 permit gases from lines 25, 26 and 27 to be supplied individually at the desired flow rate throughout the desired time interval and at the desired time, and they also make it possible for these gases to be mixed in the desired proportions.

Via sterile filter 30, line 29 is connected to pressure transducer 40 which issues an electric signal via line 41, and this signal is proportional to the pressure sensed at 28. The pressure transducer can be of type 63 95 628 E037E made by SIEMENS-ELEMA AB, Solna, Sweden.

Control unit 42 shown in FIG. 1 is connected to device 24 via lines 430a through 430l. In this control unit, which is shown in greater detail in FIG. 3, each individual miniature solenoid valve 38 is connected to an individual changeover switch 43a–43l. Each such changeover switch permits connection of the associated solenoid valve's solenoid to one of three programming units 44A, 44B or 44C, which are shown in FIG. 3, via lines A, B and C. Moreover, the changeover switch has a zero position designated 0 at which the valve is disconnected.

Each programming unit 44A–44C is provided with devices 45 and 46 that are used to select the start signal and stop signal and also with a selector switch 47 having four positions designated I, II, III and IV. At position I, valves 38 which are connected to the programming unit in question by the setting of changeover switches 43 are disconnected as a group, while at position II, these valves are continuously activated between the times determined by the start and stop signals selected by means of devices 45 and 46. At position III, valves 38 are connected to a pulse transmitter 48 so that they are activated on a pulsating basis from pulse transmitter 48 between the start time and stop time. At position IV, valves 38 are connected to pulse transmitter 49 so that they are activated on a pulsating basis from pulse transmitter 49 between the start time and stop time.

Devices 45 and 46 make it possible for the associated programming unit to be connected selectively to one—of six lines 50a–50f to which control signals are sent in the form of pulses from lines 51a–51e, of which line 51a is connected to a manually actuatable device 52 that permits a signal pulse to be issued manually, and line 51b is connected to an external device that can be used to issue signal pulses, for example a signal transmitter that issues signals in synchronism with the patient's heart rate. The other lines. 51c–51e are connected to lung ventilator 10 which is also shown in FIG. 1. For the type of lung ventilator made by Siemens-Elema AB, servoventilator 900B cited here as an example, line 51c receives a signal pulse which represents the start of the inspiration phase, line 51d receives a signal pulse which represents the start of the pause between the inspiration and expiration phases and line 51e, finally, receives a signal pulse which represents the start of the expiration phase.

The signals on lines 51a–51e can be sent to programming units 44A, 44B and 44C in different ways, and six selector switches 53a–53f are provided to select the way in which they are sent. Each of these selector switches is connected via five inputs to the lines 51a–51e respectively.

Each of selector switches 53a and 53b is connected to its own delay circuit, 54 and 55 respectively, both of which receive clock pulses via line 31, see also FIG. 1, from servoventilator 10, and they are connected to lines 50a and 50b respectively. The clock pulses on line 31 divide up a breath, i.e. a ventilation cycle, consisting of an inspiration phase, a pause and an expiration phase, into 100 equal parts or intervals, in such a way that a thumbwheel can be used to set a delay of 0–99% of the breathing cycle. In FIG. 3, a delay of 1% is set on delay circuit 54, and a delay of 78% is set on delay circuit 55.

Selector switches 53c and 53d are each connected in an analogous manner to a delay circuit, 56 and 57 respectively. Delay circuit 56 which is connected to line 50c permits the setting of a delay of 10–200 ms, and delay circuit 57 which is connected to line 50d permits the setting of a delay of 100–2000 ms. In FIG. 3, the aforesaid delay circuits are set for 50 and 500 ms respectively. Finally, it is possible to provide direct connections between lines 51a–51e and lines 50e or 50f by means of selector switches 53e and 53f respectively.

Pulse transmitter 48 is provided with a setting device 58 (thumbwheel) that is used to set the desired frequency between 1–99 Hz (set to 53 Hz in the illustration) and another setting device 59 (thumbwheel) that is used to set the portion of each period which is to be utilized actively (set to 25% in the illustration).

Pulse Transmitter 49 accepts the clock 31 from the ventilator 10. The clock 31 corresponds to the ventilation cycle of the subject. A setting device 60 (thumbwheel) is used to select a preset period corresponding to the portion of the period of clock 31 that is to be utilized by the pulse transmitter 49. The setting device 61, in turn, is used to select which portion of the preset period is to be active. Since there are one hundred parts, the setting is expressed as a percentage, and in FIG. 3, the setting is exemplified by 5% on setting device 60 and 3% on setting device 61, which means that of the five parts that are selected by means of setting device 60, only three parts are active, as selected by means of setting device 61.

Finally, control unit 42 contains measurement instrument 62 that is connected to line 41 and is used to indicate the measured pressure, and setting device 63 that is used to select the maximum permissible pressure. Means (not shown) are provided for disconnecting all miniature solenoid valves or as many of them as required to prevent the preset pressure from being significantly exceeded. This is carried out with a delay of less than 5 ms.

The aforesaid control unit 42 makes it possible to control the gas supply to line 20 with regard to gas composition and also with regard to the frequency at which gas pulses occur, the pulse-arrival time in the breathing cycle and the duration and shape of the pulses, with regard to the flow rate and/or pressure. The aforesaid control unit 42 also makes it possible to coordinate the issuing of gas pulses with the functioning of lung ventilator 10. In this connection, it shall be noted that means can be provided for indicating the amount of gas that is supplied to line 20 from each of lines 25, 26 and 27. Since the through-put per unit of time in each miniature solenoid valve is known due to the fact that the pressure drop across the valve is high relative to the pressure in line 20, the gas volume can be determined by integrating the valve-open intervals for the number of valves that are activated simultaneously.

The supply of inspired gas to the alveoli is a prerequisite for the exchanging of gas with blood in the lungs. The transport of fresh gas to the alveoli proceeds from the airway opening and is accomplished by means of convection through the airway tree. As the tree branches more and more, the collective cross-sectional area increases, and the transport speed attributable to convection decreases rapidly. The abrupt, visible increase in the aforesaid cross-sectional area at the periphery of the lungs comprises the boundary zone between fresh inspired gas and old alveolar gas. At the outermost points in the lungs, the transport of inspired gas is carried out almost exclusively by means of diffusion through this boundary zone.

During conventional respirator treatment, inspired breath volumes are utilized incompletely because of the gas which, during the previous breath participated in the gas exchange and during expiration filled the airways and tracheal duct, is returned to the alveoli initially during inspiration. The portion of fresh inspired gas which reaches far down into the lungs is thus mixed incompletely with the alveolar gas by means of diffusion, and this further limits the utilization of the inspired gas volume.

The respirator described and claimed herein permits a substantial increase in the degree of utilization of the inspired gas by providing two separate supply paths, and by providing different ways to supply inspired gas. Since the gas is supplied via line 20 during expiration, the tracheal duct and airway up to Y-tube 11 can be flushed free of previously used gas. This supply, which proceeds via line 20, can be directed as desired and pulsated so that essential parts of the patient's airways can also be flushed free of used gas. During the end of the expiration phase, the exchange of alveolar gas can also take place, thus contributing to the patient's total ventilation.

The supply of gas through line 20 can also be regulated during expiration, so that during expiration the intended pressure will be maintained in the airways, and this pressure can suitably be measured via line 29 by means of pressure transducer 40. The intended pressure during expiration can also be regulated in order to maintain a suitable lung volume that will optimize the functioning of the lung. The lung volume and the functioning of the lung can, when using a respirator like the one described in this invention, be measured in the manner described below.

The mixing of the inspired gas with alveolar gas by means of diffusion can be enhanced by means of this invention due to the fact that a pulsating flow can be supplied through line 20, which causes the gas in the lungs to oscillate and thus leads to improved forced diffusion. During expiration, the gas pulses can be formulated in such a way with regard to frequency, flow rate and pressure that they flush out the airways in the best manner, while the gas pulses occurring during inspiration can be formulated in such a way that they lead to improved diffusion in the best way.

By improving, in the aforesaid manner, the extent to which the gas in each breath is utilized, sufficient gas exchange can be achieved in the lungs at low breath volumes and thus lower pressure and less injurious effect on the lungs attributable to respirator treatment. Moreover, it is possible to avoid the aforesaid injurious effect on the airway epithelium which occurs when the lungs are ventilated using only pulses of gas at high frequency that introduce large amounts of energy into the trachea.

The analysis of gas obtained from the alveoli in order to control ventilation correctly is possible when this invention is used due to the fact that at the end of an individual inspiration, all gas flow through line 20 can be shut off so that unmixed gas from the alveoli reaches, during the next expiration, the gas analyzer 130 connected to gas analyzer receptor 13.

The gas analyzer receptor is a transducer which detects the presence and concentration of various gasses. The output of the receptor 13, in addition to being supplied to the gas analyzer 130 can be connected in a feedback fashion to control the ventilator 10. Alternatively, the output of the receptor 13 can be used to control the control unit 42.

The disadvantage entailed by the fact that parts of the lungs, as a result of long-term ventilation alone at a very high breathing frequency, collapse and thus oxygenate the blood insufficiently is avoided by the respirator described in this invention due to the fact that the lungs are exposed to a sufficiently slow breathing frequency combined with faster gas pulses so that the surface film in the alveoli, because of its time-dependent hysteresis with regard to surface tension vis-a-vis the alveolar volume, absorbs the energy that is needed in order to retain stable and uniform expansion of the lungs.

Fast adaptation of the functional mode of the respirator described herein to the pressure in the airways can be achieved by combining the respirator's design characteristics. The transmission time for pressure pulses and flow pulses can be kept low due to the fact that compact device 24 can be located close to the patient. The delay encountered in connection with a change in the functional mode is very small because of the very fast response times of the mechanical components (miniature solenoid valves 38) in device 24. These characteristics are of value due to the fact that, among other things, the respirator must be able to follow the breathing of a patient who breathes spontaneously with the support of the respirator.

In addition to the possibility of supplying anaesthetic gas in the conventional way via lung ventilator 10, the respirator which comprises this invention makes it possible, as mentioned above, to supply anaesthetic gas through line 20. The flow of anaesthetic gas through this line can be controlled by opening a specific number of miniature solenoid valves 38 in device 24, and the volume of the supplied anaesthetic gas can also be regulated by controlling the time throughout which the anaesthetic gas is supplied. Due to the fact that the anaesthetic gas is supplied only during a certain phase, immediately after the beginning of inspiration for example, all anaesthetic gas reaches the alveoli, which is a distinct advantage. As a result, the quantity of anaesthetic gas that is supplied to the alveoli, and thus the blood, can be accurately controlled. Another advantage that is gained is that all anaesthetic gas is utilized. In situations where the gas analyzer connected to receptor 13 can measure the content of anaesthetic gas, the anaesthetic gas content in the alveolar gas can also be determined in the manner mentioned above with regard to the measurement of alveolar gas. Since receptor 13 is flushed free of anaesthetic gas during inspiration, the analyzer can be reset during this period, thus eliminating the need for special resetting devices and measures. The statements set forth above regarding anaesthetic gas also apply to gases having effects other than anaesthetic such as gases that are therapeutically active.

The respirator disclosed and claimed herein permits the functioning of the lungs and circulation organs to be studied in great detail. Test gas can be supplied with precision through channel 20 with regard to a particular time in the breathing cycle and to volume. The analyzer connected to receptor 13 is required to analyze the gases included in the test gas. By studying the dilution of a given amount of test gas that is not dissolved in physiological fluids, sulphur hexafluoride, $SF_6$, for example, the volume of alveolar gas can be determined. If the test gas also contains carbon monoxide, CO, the diffusion capacity of the lungs can be determined in accordance with principles which are otherwise known in and of themselves. By studying the extent to which one or more soluble gases remain in the body beyond the point which calculations show can be attributed to dilution in the alveolar gas, one can determine the flow of blood through the lung capillaries which, as a rule, is approximately the same as the heart's minute volume. One can also determine the quantity of fluid in the lungs. Supplying pulses of test gas which can be made to occur during different parts of the inspiration phase for different breaths and then measuring the cycle during the following expiration permits accurate studies to be made of the way in which the different parts of the inspiration volume reach functioning parts of the lungs. From these data, information can be obtained regarding the functioning of both the airway and lung blood circulation.

The version of the respirator described in accordance with this invention can be modified within the scope of the patent claims which follow while retaining the advantages and possibilities offered by the respirator's functions and utilization as described above.

We claim:

1. A respirator for use with a supply of a respiratory gas, and with a supply of a separate breathable gas, for connection to airways of human or animal subjects having lungs, the respirator comprising in combination:

a first ventilator adapted for connection to the supply of respiratory gas and having first means communicating with the airways of the subject for supplying a flow of respiratory gas from the supply of respiratory gas to, and receiving exhaled respiratory gas from, the airways of the subject for ventilating the lungs of the subject in a normal respiratory pattern to simulate spontaneous breathing;

a second ventilator adapted for connection to the supply of the separate breathable gas and having second means communicating with the airways of the subject for supplying the separate breathable gas to the airways of the subject, for inspiration by said subject, independently of said flow of respiratory gas, said second means communicating with the airways of the subject having at least one line for supplying the separate breathable gas under pressure, said second ventilator further having a plurality of valves connected to said at least one supply line and adapted for parallel connection between said at least one line and the supply of the separate breathable gas, said plurality of valves being individually actuatable via control signals for providing high frequency pulsating flow of the separate breathable gas to said at least one line; and a control unit connected to said plurality of valves in said second ventilator for generating said control signals to said plurality of valves, said control unit having means for setting selected characteristics of said high frequency pulsating flow of the separate breathable gas by varying said control signals.

2. The respirator of claim 1 wherein said first ventilator includes a plurality of output signal lines respectively supplying output signals identifying selected points in a ventilation pattern of the subject and wherein said control unit is connected to said signal lines to receive said plurality of output signals, said control signals generated by said control unit being dependent on said plurality of output signals for regulating said plurality of valves in coordination with said ventilation pattern of the subject.

3. The respirator of claim 2, wherein said first means communicating with the airways of the subject includes a tracheal tube having an open end, said respirator further comprising a pressure transducer for monitoring pressure at said open end of said tracheal tube, said pressure transducer generating electrical signals corresponding to pressure at said open end of said tracheal tube.

4. The respirator of claim 1 further comprising at least one distributor in said second ventilator adapted for connection to the supply of the separate breathable gas and to which a selected number of said plurality of valves are connected.

5. The respirator of claim 4 further comprising a pressure regulator adapted for receiving the separate breathable gas under pressure from the supply of the separate breathable gas, said pressure regulator having an output connected to said distributor for supplying the separate breathable gas therethrough to said distributor.

6. The respirator of claim 1 wherein each valve of said plurality of valves has a narrow flow channel.

7. The respirator of claim 1 further comprising a gas analyzer receptor connected to said first ventilator to receive gas communicated to and from the airways of the subject for monitoring gas concentration levels of gas supplied to and received from the airways of the subject.

8. The respirator of claim 7 wherein said gas analyzer receptor is disposed at said first means communicating with the airways of the subject.

9. The respirator of claim 1 wherein said second means communicating with the airways of the subject includes a means for humidifying the separate gas as the separate gas is supplied to the airways of the subject.

10. The respiratory of claim 1 further comprising means,, connected to said second means communicating with the airways of the subject for adding pharmaceutically active substances to the separate gas.

11. A respirator for connection to airways of human or animal subjects for use with a first gas supply containing a respiratory gas, and a second gas supply containing a separate breathable gas comprising:
a lung ventilator connected to a tracheal tube adapted for insertion in the airways of the subject, said lung ventilator further adapted for connection to the first gas supply for supplying the respiratory gas to and receiving exhaled respiratory gas from the airways of the subject;
a gas supply means having an outlet disposed in said tracheal tube and adapted for connection to the second gas supply for supplying the separate breathable gas to the airways of the subject via said outlet simultaneously with and independently of said respiratory gas, said gas supply means having a plurality of electronically operated valves connected to said outlet and adapted for connection in parallel between the second gas supply and said outlet; and
a control unit connected to said plurality of electronically operated valves in said gas supply means for operating said plurality of electronically operated valves to pulsate the separate breathable gas at a high frequency as it is supplied to the airways of the subject, said control unit having selection means for setting selected characteristics of said pulsated separate breathable gas supply.

12. The respirator of claim 11 wherein said plurality of electronically operated valves are solenoid valves.

13. The respirator of claim 11 wherein said gas supply means further comprises a distribution bank adapted for receiving a supply of gasses from a plurality of gas sources and distributing said supply of gasses to a plurality of outputs respectively connected to said plurality of electronically operated valves.

14. The respirator of claim 11 wherein said control unit comprises a plurality of programming units selectively connectible to each of said plurality of electronically operated valves for operating said plurality of electronically operated valves in accordance with a selected one of a plurality of operating programs.

15. The respirator of claim 14 wherein said lung ventilator includes a plurality of control signal lines respectively supplying control signals identifying selected points of a ventilation cycle of the subject and wherein at least one of said plurality of programming units is connected to said lung ventilator control Signal lines for receiving said control signals therefrom to control operation of said plurality of electronically operated valves.

16. The respirator of claim 15 wherein said control unit comprises at least one delay unit interconnected between said at least one of said plurality of programming units and said lung ventilator for delaying transmittal of said control signals to said at least one of said plurality of programming units by a selected delay time.

17. The respirator of claim 15 wherein said control unit further comprises at least one selector switch interconnected between said at least one of said plurality of programming units and said lung ventilator for selecting one of said control signals for transmittal to said at least one of said plurality of programming units.

18. The respirator of claim 14 wherein said control unit further comprises a manually operable single pulse actuator connected to at least one of said plurality of programming units for supplying a single pulse of the separate breathable gas to the airways of the subject.

19. The respirator of claim 14 wherein said control unit further comprises a plurality of changeover switches respectively interconnected between each of said plurality of programming units and each of said plurality of electronically operated valves for selecting one of said plurality of programming units for controlling operation of selected ones of said plurality of electronically operated valves.

20. The respirator of claim 14 wherein said control unit further comprises at least one pulse transmitter means connected to at least one of said plurality of programming units for generating control pulses of selected frequency and duration, said control pulses being connectible to said plurality of electronically operated valves for controlling said plurality of electronically operated valves to pulsate the separate gas supplied to the airways of the subject.

21. The respirator of claim 14 wherein said control unit further comprises a pulse transmitter connected to receive a control signal from said lung ventilator, said pulse transmitter connected to at least one of said plurality of programming units for generating control pulses of selected frequency and duration, said control pulses being connectible to said plurality of electronically operated valves for controlling said plurality of electronically operated valves to pulsate the separate breathable gas supplied to the airways of the subject.

* * * * *